(12) United States Patent
Fisher et al.

(10) Patent No.: US 6,519,076 B2
(45) Date of Patent: Feb. 11, 2003

(54) METHODS AND APPARATUS FOR OPTICAL IMAGING

(75) Inventors: Walter G. Fisher, Knoxville, TN (US); Eric A. Wachter, Oak Ridge, TN (US)

(73) Assignee: Photogen, Inc., Knoxville, TN (US)

( * ) Notice: Subject to any disclaimer, the term of this patent is extended or adjusted under 35 U.S.C. 154(b) by 0 days.

(21) Appl. No.: 10/045,562

(22) Filed: Jan. 10, 2002

(65) Prior Publication Data

US 2002/0122236 A1 Sep. 5, 2002

Related U.S. Application Data

(60) Division of application No. 09/779,808, filed on Feb. 8, 2001, which is a continuation-in-part of application No. 09/072,962, filed on May 5, 1998, now Pat. No. 6,096,036, which is a division of application No. 08/741,370, filed on Oct. 30, 1996, now Pat. No. 5,832,931, and a division of application No. 09/096,832, filed on Jun. 12, 1998, which is a continuation-in-part of application No. 08/739,801, filed on Oct. 30, 1996, now Pat. No. 5,829,448.
(60) Provisional application No. 60/187,958, filed on Mar. 9, 2000.

(51) Int. Cl.[7] .............................. G02F 01/35; G02F 1/01
(52) U.S. Cl. ........................................ 359/326; 359/278
(58) Field of Search ................................ 359/278, 239, 359/276; 342/27, 128; 345/157; 367/100; 250/338.5; 356/437

(56) References Cited

U.S. PATENT DOCUMENTS

| | | | |
|---|---|---|---|
| 3,868,950 A | 3/1975 | Kato | 601/156 |
| 3,986,513 A | 10/1976 | Stuhl | 607/91 |
| 4,172,979 A | 10/1979 | Morrison | 378/65 |
| 4,444,189 A | 4/1984 | Seiverd | 607/91 |
| 4,691,332 A | 9/1987 | Burstein | 378/7 |
| 4,767,195 A | * | 8/1988 | Pepper | 359/276 |
| 4,856,528 A | 8/1989 | Yang et al. | 382/131 |
| 5,008,907 A | 4/1991 | Norman et al. | 378/65 |
| 5,034,613 A | 7/1991 | Denk et al. | 250/458.1 |
| 5,053,006 A | 10/1991 | Watson | 604/20 |
| 5,257,202 A | 10/1993 | Feddersen et al. | 702/32 |
| 5,368,031 A | 11/1994 | Cline et al. | 600/411 |
| 5,445,608 A | 8/1995 | Chen et al. | 604/20 |
| 5,462,053 A | 10/1995 | Biggs et al. | 424/9.32 |
| 5,579,773 A | 12/1996 | Vo-Dinh et al. | 600/317 |
| 5,622,946 A | 4/1997 | Sessler et al. | 514/185 |

(List continued on next page.)

OTHER PUBLICATIONS

PCT International Search Report re application no. PCT/US01/07231, dated Jul. 13, 2001.
Denk et al, "Two–Photon Molecular Excitation in Laser–Scanning Microscopy," *Handbook of Biological Confocal Microscopy*, 2nd edition, J.B. Pawley, ed., pp. 445–458, 1995.
Wachter, et al, "A Quadrature Detection Scheme for Pulsed Ion–Cyclotron Resonance Mass Spectroscopy," Int'l J. Mass Spec. & Ion Proc., vol. 103, pp. 169–179, 1991.

*Primary Examiner*—Ricky Mack
*Assistant Examiner*—Omar Hindi
(74) *Attorney, Agent, or Firm*—Cook, Alex, McFarron, Manzo, Cummings & Mehler, Ltd.

(57) ABSTRACT

Methods and apparatus directed to using modulation to substantially improve detection limits in optical imaging, and to substantially improve the performance of various optical imaging systems. In an illustrative embodiment, such modulation is achieved using a modulated light source, a modulation frequency reference, a detector, and a demodulator. The modulated light source may comprise a light source emitting an inherently modulated output; alternately, this modulated light source may comprise a separate optical modulator and a continuous wave, modulated, or pulsed light source configured so as to impose a modulation in the output of light source. Methods for imagine using such modulation are also disclosed.

19 Claims, 5 Drawing Sheets

U.S. PATENT DOCUMENTS

| | | | |
|---|---|---|---|
| 5,632,970 A | 5/1997 | Sessler et al. | 424/9.61 |
| 5,645,816 A | 7/1997 | Unger | 424/9.34 |
| 5,654,423 A | 8/1997 | Kahl et al. | 540/145 |
| 5,702,683 A | 12/1997 | Smith et al. | 424/10.03 |
| 5,706,810 A | 1/1998 | Rubinsky et al. | 600/412 |
| 5,745,437 A | 4/1998 | Wachter et al. | 367/100 |
| 5,832,931 A | 11/1998 | Wachter et al. | 128/898 |
| 5,845,639 A | 12/1998 | Hochman et al. | 600/407 |
| 5,889,490 A | 3/1999 | Wachter et al. | 342/127 |
| 5,969,663 A * | 10/1999 | Fullerton et al. | 342/27 |
| 6,407,846 B1 * | 6/2002 | Myers et al. | 359/239 |

* cited by examiner

METHODS AND APPARATUS FOR OPTICAL IMAGING

This application is a divisional of copending U.S. application Ser. No. 09/779,808 filed on Feb. 8, 2001 which is based provisional application no. 60/187,958 filed Mar. 9, 2000 and which is a continuation-in-part of U.S. Ser. No. 09/072,962, filed May 5, 1998, now U.S. Pat. No. 6,096,036, which is a divisional of application Ser. No. 08/741,370, U.S. Pat. No. 5,832,931 (issued Nov. 10, 1998), filed Oct. 30, 1996, and U.S. Ser. No. 09/096,832, filed Jun. 12, 1998, which is a continuation-in-part of U.S. application Ser. No. 08/739,801, now U.S. Pat. No. 5,829,448 (issued Nov. 3, 1998), filed Oct. 30, 1996.

BACKGROUND OF THE INVENTION

The present invention is a continuation in part of U.S. Ser. No. 09/072,962, filed May 5, 1998 ("Method For Improved Selectivity In PhotoActivation and Detection of Molecular Diagnostic Agents"), which is a divisional of U.S. Pat. No. 5,832,931 (issued Nov. 10, 1998), filed Oct. 30, 1996, and U.S. Ser. No. 09/096,832, filed June 12, 1998 ("Improved Method and Apparatus For Multi-Photon Photo-Activation of Therapeutic Agents"), which is a continuation-in-part of U.S. Pat. No. 5,829,448 (issued Nov. 3, 1998), filed Oct. 30, 1996, which are incorporated herein by reference in their entirety.

The present invention is directed to an apparatus and methods for imaging using modulated light.

The quality of images obtained using, and operational usefulness of, many scientific and medical imaging systems, and in particular optical or laser based imaging systems, can be significantly degraded by various instrumental or ambient noises or interferences, such as those caused by stray light, electronic noise, or other optical or electronic interference. Such noises include continuous or semi-continuous background or noise sources, such as interferences from noise sources such as room light or electronic noise at specific frequencies, for example from a nearby electric motor, and broadband or "pink noise" sources. The measurement environment, along with the electronics and other devices used for any measurement, contributes broadband noise, sometimes called pink noise, into any measurement. This noise can be particularly severe at low frequency, f, due to the well known 1/f properties of such noise.

U.S. Ser. No. 09/072,962 teaches that at least some of these noises or interferences can, in some of these imaging systems and under certain conditions, be significantly reduced through use of certain modulation methods. However, more generally applicable noise reduction methods would allow extension of this modulation concept to other systems and other applications.

Further, while the use of various modulation methods for reduction of interference to improve detection performance for measurements has been generally done in other fields, the present inventors are unaware of the use of modulation and demodulation, as in the present invention, in the various fields of optical imaging, and in particular for use in various optical or laser based systems for scientific and medical imaging. Hence, it is an objective of the present invention to use such methods and apparatus in such fields to overcome the problems caused by such noises and interferences.

SUMMARY OF THE INVENTION

The present invention relates to and is directed toward methods and apparatus using a modulated light source and associated circuitry and modulation schemes to substantially improve detection limits in optical imaging and to substantially improve the performance of various optical imaging systems. One way that such methods and apparatus achieve such improvement is by moving the detected signal to a quiescent part of the electromagnetic spectrum. This approach results in suppression of most noise from continuous or semi-continuous background or noise sources and also causes minimization of the effects of pink noise. Modulation methods applicable with the present invention include amplitude modulation, phase modulation, and frequency modulation.

In an illustrative embodiment, the present invention is directed to an apparatus comprising a modulated light source, a modulation frequency reference, a detector and a demodulator. This apparatus may function independently of or in conjunction with an imaging system, such as for example a microscope or other imaging devices as explained infra, and a data acquisition system. The demodulator may comprise, for example, a lock-in amplifier, a dual-phase lock-in amplifier, a heterodyne or superheterodyne demodulator, a quadrature heterodyne or quadrature superheterodyne demodulator, or similar phase-sensitive demodulation unit.

In a further embodiment, the modulated light source comprises a light source emitting an inherently modulated output. Alternatively, the modulated light source may comprise a separate optical modulator and a continuous wave, modulated, or pulsed light source configured so as to impose a modulation in the output of the light source. This modulated light source, modulation frequency reference, detector, and demodulator may function in conjunction with an imaging system and a data acquisition system or other similar hardware to enable collection of imaging data or multi-dimensional images of a sample.

The present invention is also directed to methods using modulation to substantially improve detection limits in optical imaging, and the performance of various optical imaging systems. Some of these methods use the apparatus described above.

The present invention is also directed to a method for imaging a material, the method comprising the steps of:
encoding light from a light source with a modulation pattern to produce a modulated light;
directing said modulated light onto or into said material, said material emitting a modulated optical signal which is characteristic of the material;
detecting said emitted modulated optical signal from the material and converting the optical signal into a modulated electronic signal which is characteristic of the material; and
demodulating the modulated electronic signal which is characteristic of the material The present invention can be used in a number of fields, including: various single-photon, two-photon and multiphoton excited microscopes and optical imaging devices and imaging systems based on transmission, absorption, reflection, scatter or luminescence based phenomena; laser scanning microscopes; confocal microscopes; optical coherence tomography systems; terahertz imaging systems; and various scanning probe optical microscopes. This list of fields, however, is merely illustrative, as one skilled in the art upon reading the present application would understand that other fields are also contemplated for the present invention.

BRIEF DESCRIPTION OF THE DRAWINGS

The above and other features and advantages of the present invention will become further apparent from the following detailed description of example embodiments of the present invention in conjunction with the drawings in which.

DETAILED DESCRIPTION OF THE PRESENTLY PREFERRED EMBODIMENTS

Figure 1:
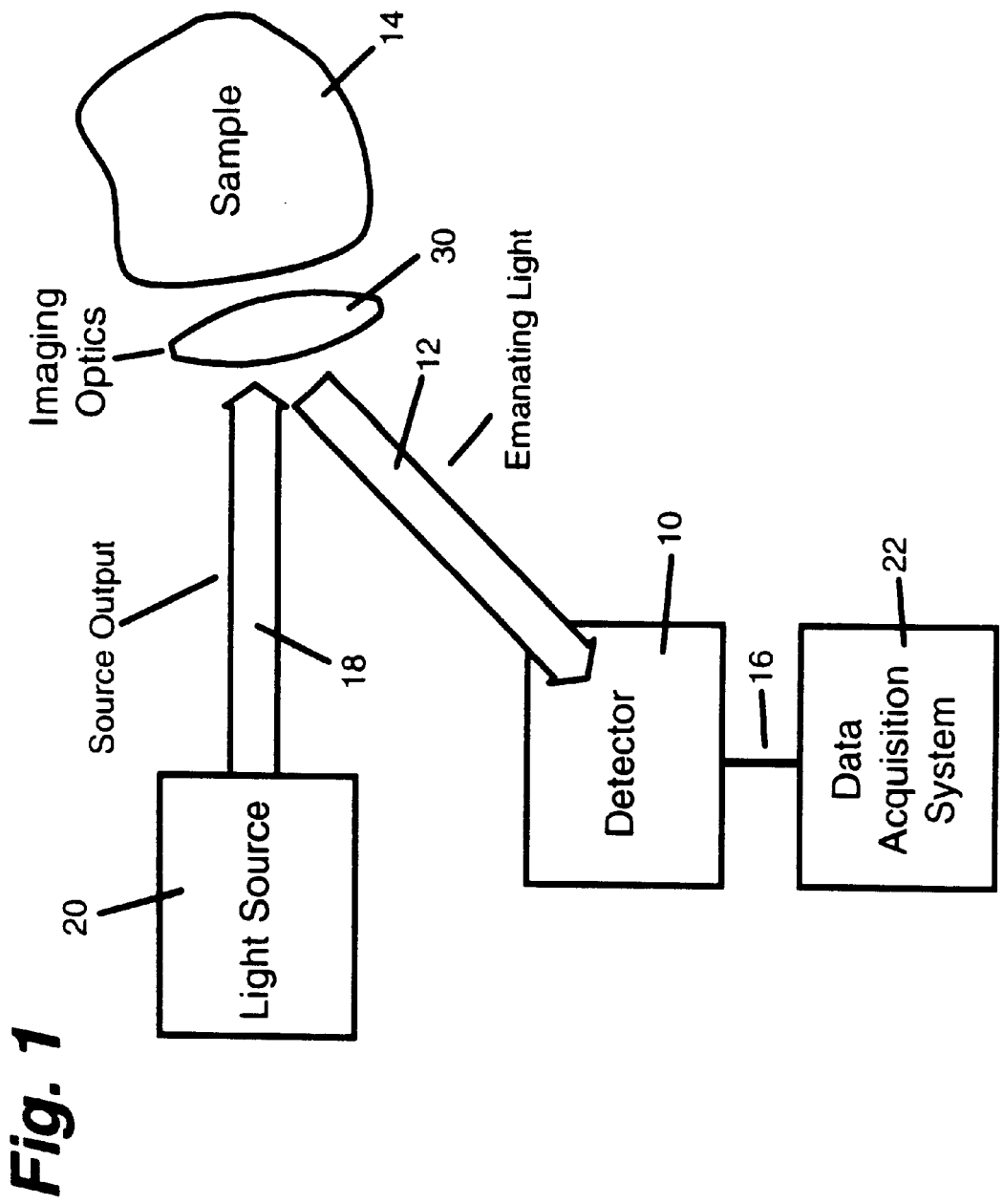
FIG. 1 illustrates components of a typical optical imaging system.

FIG. 1 illustrates a typical optical imaging system. As shown in FIG. 1 typical detection schemes used in optical microscopy and imaging, and especially in many scanning optical microscopy and imaging systems, use an optical detector 10 to detect light energy 12 emanating from a sample 14 and to convert this energy into a measurable electronic signal 16. By scanning illumination light 18 from a light source 20 on or around the sample, scanning the portion of the sample visible to the detector, or scanning both the source and detector synchronously, this electronic data can be acquired as a function of sample location. This spatially-encoded data is subsequently processed to produce an image of the sample. Typically, such data is acquired using a computer-based data acquisition system 22 that samples the detector data at a sampling frequency equal to or greater than the scanning frequency. Such an approach, however, suffers from a number of disadvantages.

In particular, prior to data acquisition, the electronic output of the detector in such schemes is generally sent to a high-gain amplifier that provides low pass filtering with a bandwidth chosen to match the maximum data acquisition frequency (this is commonly on the order of 100 kHz). The output of this amplifier is sampled using an analog-to-digital converter (ADC) or similar apparatus, which provides digital data used for image processing. In such an arrangement, any noise present, from dc (i.e., 0 Hz) to 100 kHz will be detected, amplified, sampled, and incorporated into the image.

The detection limit of such imaging is generally defined to be a signal-to-noise ratio $(S/N) \geq 3$, where S is the statistical mean of the analytical signal and N is the standard deviation) of the measurement. However, when making a measurement in the presence of a measurable background, a more appropriate equation for the detection limit is $(S-B)/N_B \geq 3$, where B is the mean of the background and $N_B$ is the standard deviation of the background. Improving the detection limit requires either increasing the signal or decreasing the noise associated with the measurement as well as decreasing background levels. Unfortunately the conventional detection schemes commonly used in optical imaging are inefficient at reduction of background. For example, ambient lighting (which emits light as a continuous, or substantially continuous low frequency, optical background), electronic noise at specific frequencies within the bandwidth of the detection system, and pink noise (which can be particularly severe at the relatively low frequencies used in such schemes due to the 1/f phenomenon), all contribute to background in optical measurements obtained using such schemes.

The inventors of the present invention have discovered a number of uses and apparatus which employ amplitude, phase or frequency modulated light sources or modulation schemes, such as those described in the examples and embodiments below that substantially improve detection limits in such optical imaging and improve the performance of such optical imaging systems by moving the analytical signal to a quiescent part of the electromagnetic spectrum. For example, the inventors have discovered that, instead of detection at dc frequencies (or substantially similar, low frequencies), the analytical signal can be modulated at a relatively high frequency (for example, by modulating the amplitude of the illuminating light source), and a phase sensitive detector (PSD, such as, for example, a lock-in-amplifier, LIA), used to selectively recover signals emanating from the sample at this modulation frequency. Using this approach, most noise from continuous or semi-continuous background or noise sources is substantially eliminated from the measurement since signal components originating from such sources, such as, for example, those from an interfering light source, occur at electronic frequencies outside the detection bandwidth of the PSD and therefore will not be detected by the PSD. Furthermore, by limiting the detection bandwidth and moving the bandwidth to relatively high frequencies, the methods and apparatus of the present invention minimize the effects of pink noise.

EXAMPLE EMBODIMENTS

Figure 2:
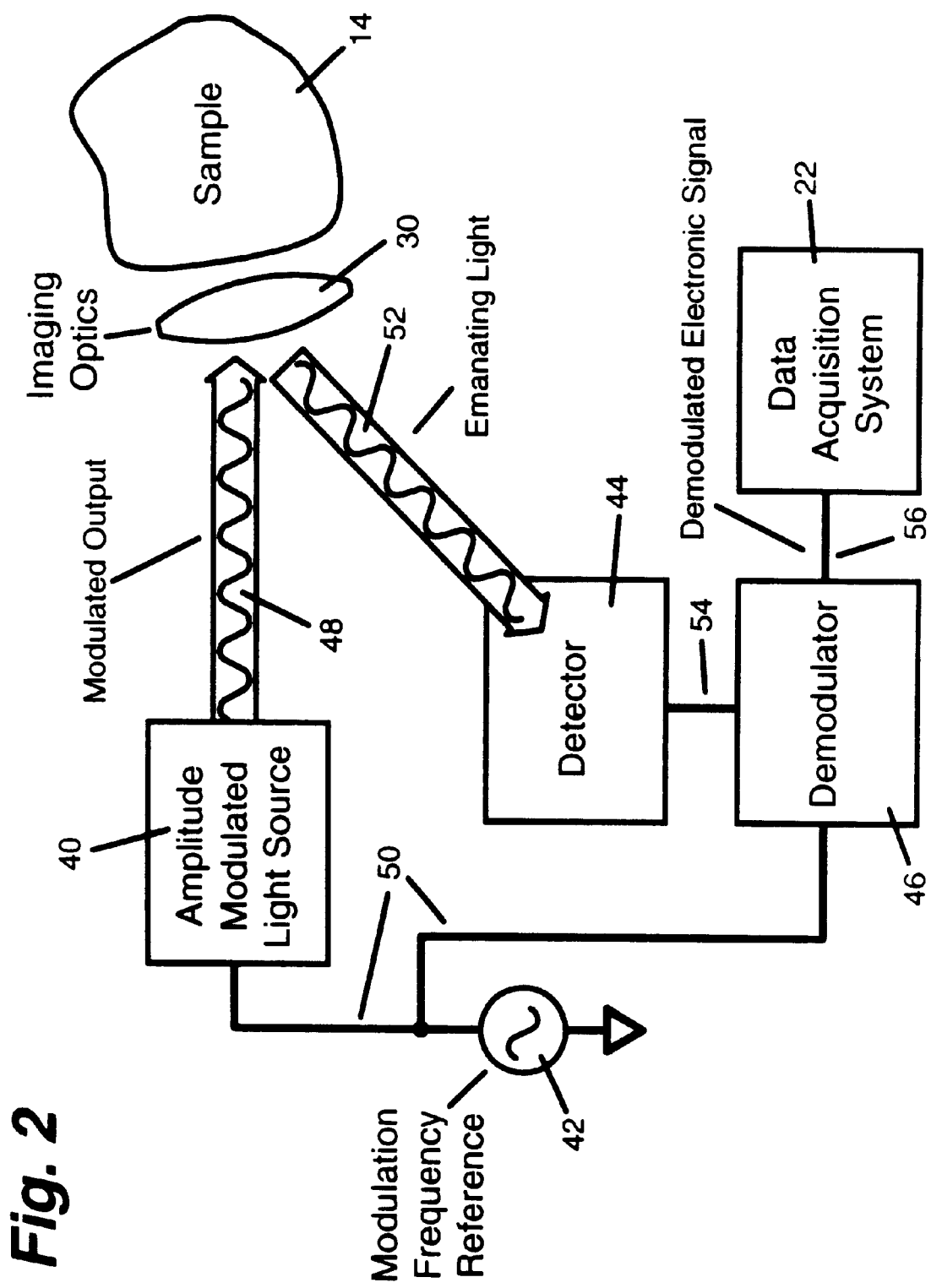
FIG. 2 illustrates an example embodiment of the present invention comprising an amplitude modulated light source, a modulation frequency reference, an imaging system, a detector, a demodulator, and a data acquisition system.

A first example embodiment of the methods and apparatus of the present invention is illustrated in FIG. 2. As shown in FIG. 2, the apparatus of this embodiment includes an amplitude modulated light source 40, a modulation frequency reference 42, imaging optics 30 (such as, for example, a microscope, telescope, camera or other imaging optics or imaging device), a detector 44, a demodulator 46 (such as, for example, a lock-in amplifier, dual-phase lock-in amplifier, heterodyne or superheterodyne demodulator, or similar phase-sensitive demodulation unit), and a data acquisition system 22. The amplitude modulated light source 40 can produce an inherently modulated output 48 (such as, for example, that produced by a pulsed or modulated lamp or pulsed or modulated laser), as shown in FIG. 1. In an alternate example embodiment illustrated in FIG. 3, the amplitude modulated light source 40 can include a separate optical modulator 60 (such as, for example, a photoelastic modulator, acousto-optic modulator, electro-optic modulator, pockels cell, or other type of mechanical or electronic chopper or modulator) configured so as to introduce an amplitude modulation in the output 62 of a continuous wave, modulated, or pulsed light source 64. The amplitude modulated light source 40 of either embodiment is connected to the modulation frequency reference 42. The amplitude modulated light source may thereby either be modulated in response to a reference frequency signal 50 issued by the modulation frequency reference 42, or man issue a reference frequency signal 50 to the modulation frequency reference 42. More specifically, the amplitude modulated light source may emit a reference frequency, i.e., serve as a master frequency source for the modulation frequency reference, or alternately, the amplitude modulated light source may be slaved to a reference frequency provided by the modulation frequency reference. Each is contemplated in the present invention.

Preferably, the modulated output of the amplitude modulated light source is directed into the imaging optics 30, which serve to direct a portion of light from the light source 40 onto or into a sample 14 (i.e., to illuminate the sample with an illuminating light). Light subsequently emanates from said sample and is collected by the imaging optics 30. This collection may be confocal or non-confocal with said illuminating light. A portion of such light emanating from the sample results from the interaction of the illuminating light with the sample as a result of, for example: transmission; absorption; reflection, elastic or inelastic scatter, including Mie or Raman scattering; or luminescence, such as fluorescence, phosphorescence, and chemiluminescence, including single-photon induced fluorescence and single-photon, two-photon or multi-photon laser induced fluorescence. Because such interaction typically occurs on a time frame that is substantially comparable with or shorter than anticipated modulation frequencies (which might, for example be as high as about 1 GHz, or 1 ns in period), the portion of light emanating from the sample resulting from the interaction of the illuminating light with the sample will thereby be encoded with an amplitude modulation at the modulation frequency, or at a multiple of the modulation frequency, that will be synchronous with the amplitude modulated light source.

This portion of light 52 emanating from the sample is directed to a detector 44 (such as, for example, a photomultiplier tube, microchannel plate device, photodiode, avalanche photodiode, charge coupled device or charge coupled device array, or charge injection device or charge injection device array), and thereby converted from a modulated optical signal into a modulated electronic signal 54. In the methods and apparatus of the present invention, it is only necessary that a small portion, which man be from nearly 100% to approximately 1% or less, of the total electronic signal 54 result from detection of the modulated optical signal. This is advantageous, as frequently the total light impinging upon the detector, and the total electronic signal emanating from the detector, may not result entirely and solely from detection of the modulated optical signal (for example, the total light impinging upon the detector may include substantial continuous or semi-continuous background light not resulting from interaction of the illuminating light with the sample, and the total electronic signal emanating for the detector may include substantial pink noise or other interference not resulting from conversion of the emanating illuminating light into a modulated electronic signal). The electronic signal 54 is directed into a demodulator 46, which uses the reference frequency signal 50 issued by the modulation frequency reference 42 to generate a demodulated electronic signal 56 that is issued to a data acquisition system 22. The data acquisition system may, via conventional means, cooperate with the imaging optics or other similar hardware to enable collection of one or more demodulated electronic signals resulting from interaction of the amplitude modulated light source with various portions of the sample, and may thereby enable collection of imaging data or multi-dimensional images of the sample.

The salient features of the present invention will be further clarified by the following examples which are meant to illustrate, and not limit, the present invention.

Example 1—Extracavity Modulated Laser Light Source in Microscopy

Lasers or other intense light sources are frequently used to illuminate samples for microscopic examination. Such illumination may be achieved via transmissive or retroreflective (i.e., epi-illumination) illumination methods. For example, Denk et al. (U.S. Pat. No. 5,034,613) describe use of a mode-locked laser (with a pulse repetition frequency of approximately 80 MHz) and scanning epi-illumination microscopy system for acquisition of two- or three-dimensional images of living cells and tissue samples (i.e., two-photon laser scanning microscopy). This microscope is used to excite molecular fluorophors added to or present in biological specimens. The resultant emitted fluorescent light is collected by the excitation objective using an epi-illumination configuration. The collected light is detected by a detector and data acquisition system without use of demodulation methods. In a later, related work, Denk et al. (W. Denk, D. W. Piston and W. W. Webb, "Two-Photon Molecular Excitation in Laser-Scanning Microscopy," in Handbook of Biological Confocal Microscopy, Second Edition, J. B. Pawle, ed., Plenum Press, New York, 1995, pp. 445–458) recognized that such systems are "vulnerable to contamination from ambient room light." Notably, no effective method for combating such contamination was proposed.

Figure 3:
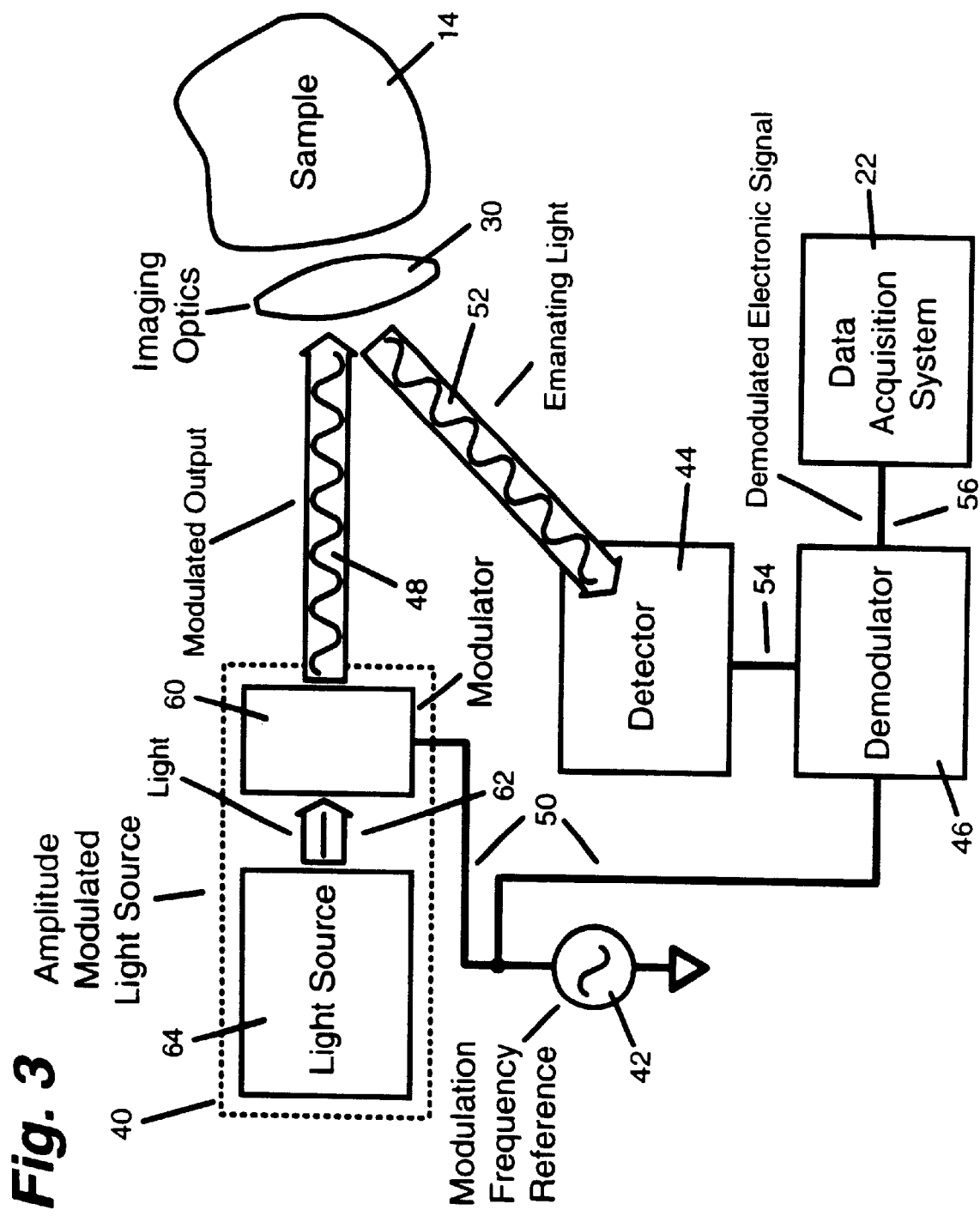
FIG. 3 illustrates an alternate example embodiment of the present invention wherein the amplitude modulated light source includes a separate optical modulator.

The present inventors have constructed a number of two-photon laser scanning imaging systems, and found that, without use of modulation and demodulation methods, such systems are highly vulnerable to contamination from ambient room light and other noise sources. However, by addition of a modulator, modulation frequency reference, and demodulator, according to the methods and apparatus of the present invention, as illustrated in FIGS. 2 and 3, the effects of such contamination can be substantially eliminated.

Specifically, in this example, the inventors used optical chopping (using one time a photoelastic modulator, operating at <100 kHz modulation frequency, and another time a electro-optical modulator, operating at <10 MHz modulation frequency), to impart an amplitude modulation on the output of the laser light source prior to illumination of a sample. Interaction of this modulated light with the sample thereby results in stimulation of a two-photon excited fluorescent emission from the sample that is synchronously modulated with the illumination light. Demodulation of the resultant detector signal (using one time a lock-in amplifier and another time a dual-phase lock-in amplifier) prior to data acquisition allows background noise and other interference, such as contamination of detector signals from ambient room light, to be electronically rejected.

Data from this example for the apparatus and method described above are shown intra in TABLE 1, which compares imaging results (signal-to-noise ratio, i.e., $(S-B)/N_B$) obtained using an extracavity modulated laser light source (modulated at 47 kHz) and commercial lock-in amplifier demodulation, as taught in the present invention, versus results obtained using conventional dc or direct detection (i.e., as taught by Denk et al.). Data was collected under conditions of (1) no optical background and (2) severe, continuous optical background (DC Background). In both cases, a significant advantage is noted for the modulated methods and apparatus, particularly in the presence of background.

Thus, this example illustrates that the performance of new or existing imaging devices and systems, such as the two-photon laser scanning microscope or other imaging systems, can be significantly enhanced by incorporation of the modulation and demodulation methods and apparatus of the present invention.

Example 2—Use of Modulated Light Sources for Imaging

Extracavity amplitude modulation, as discussed in Example 1, is practical for modulation at frequencies up to about 10 MHz, but can become unacceptably complex and expensive for higher modulation frequencies. Since it is often desirable to have a high imaging scan rate (for example, 100 kHz or greater) to minimize image acquisition time, and since it will often be desirable to use a light source that is modulated at a frequency that is 10- to 100-fold or more higher than this scan rate (so as to maximize selectivity of the demodulation process) operation at such high scan rates makes modulation frequencies of 10 MHz or greater desirable.

Fortunately, some light sources applicable to various imaging applications are inherently modulated, or can be readily modulated, at very high frequencies (for example, at frequencies up to or above 100 MHz). Examples of such inherently modulated light sources include various mode-locked lasers. Other sources are readily modulated with minimal difficulty. For example, many diode lasers are readily modulated by imparting an amplitude modulation on their drive signal. Hence, many of these inherently or readily modulated light sources are well suited to various imaging applications using the present invention.

To illustrate this use, the inventors of the present invention have further modified the two-photon laser scanning imaging system described in Example 1. The mode-locked laser source used in the system of this example has an inherently pulsed output, with a pulse repetition frequency of approximately 70 MHz. This 70 MHz pulsed output was thus used as the modulated output (i.e., output of an amplitude modulated light source) in a system comparable to that illustrated in FIG. 2. Notably, no additional modulation apparatus was necessary. This modulated output was used to excite a sample containing a fluorescent dye having a fluorescence lifetime less than the period of the laser pulse train (i.e., $\tau < [1/(\text{pulse repetition frequency})]$; note that it is generally desirable to assure that the period of the modulated light source is comparable to or less than the lifetime, $\tau$, of the phenomenon probed with such light source in order to avoid saturation of said phenomenon). The laser was also used to produce a reference frequency signal (this was obtained by directing of small portion of the laser output onto a fast photodiode detector). Illumination of the sample with this pulsed laser light resulted in stimulation of two-photon excited fluorescent emission from the sample, wherein such emission exhibited synchronous modulation with the pulsed laser light. Because the fluorescence lifetime of the fluorophore used in this example is less than the time between sequential pulses of the laser, the fluorescent signal thereby generated decays between laser pulses and thus occurs as a periodic signal at, and synchronous with, the mode-locked frequency. Demodulation of the resultant detector signal (using a commercial high-frequency lock-in amplifier) prior to data acquisition caused background noise and other interference, such as contamination of detector signals from ambient room light, to be electronically rejected.

Data from this example for the apparatus and method described above are also shown in TABLE 1, which compares imaging results obtained using an inherently modulated laser light source (modulated at 70 MHz) and commercial high-frequency lock-in amplifier demodulation with that obtained using conventional dc or direct detection. Data was collected under conditions of (1) no optical background and (2) moderate, continuous optical background (DC Background). While similar results were obtained in the absence of background, a clear advantage is evident for the modulated apparatus in the presence of background.

Thus, this example further illustrates that the performance of new or existing imaging devices and systems, such as, for example, the two-photon laser scanning microscope or other imaging systems, can be significantly enhanced by incorporation of the modulation and demodulation methods and apparatus of the present invention.

Example 3—Use of Heterodyne Demodulators

The present inventors have discovered that in many cases, the features (and resultant high cost) of standard, commercial lock-in amplifiers or similar equipment are unnecessary for implementation of the present invention. Furthermore, since such equipment is generally designed to operate over a wide range of modulation frequencies, using such equipment for electronic measurement at a specific modulation frequency is inefficient. The present invention, however, is able to overcome these problems. In particular, the inventors have discovered that it is relatively simple and inexpensive to build a dedicated demodulation apparatus that is highly optimized for a single modulation frequency or small range of frequencies. An example of such demodulation apparatus is the heterodyne or superheterodyne demodulator, such as that used in common portable radios. Such circuitry, or substantially equivalent or comparable circuitry, can provide a simple, low cost, and extremely, high performance demodulator suitable for processing of image data according to the methods and apparatus of the present invention.

Figure 4:
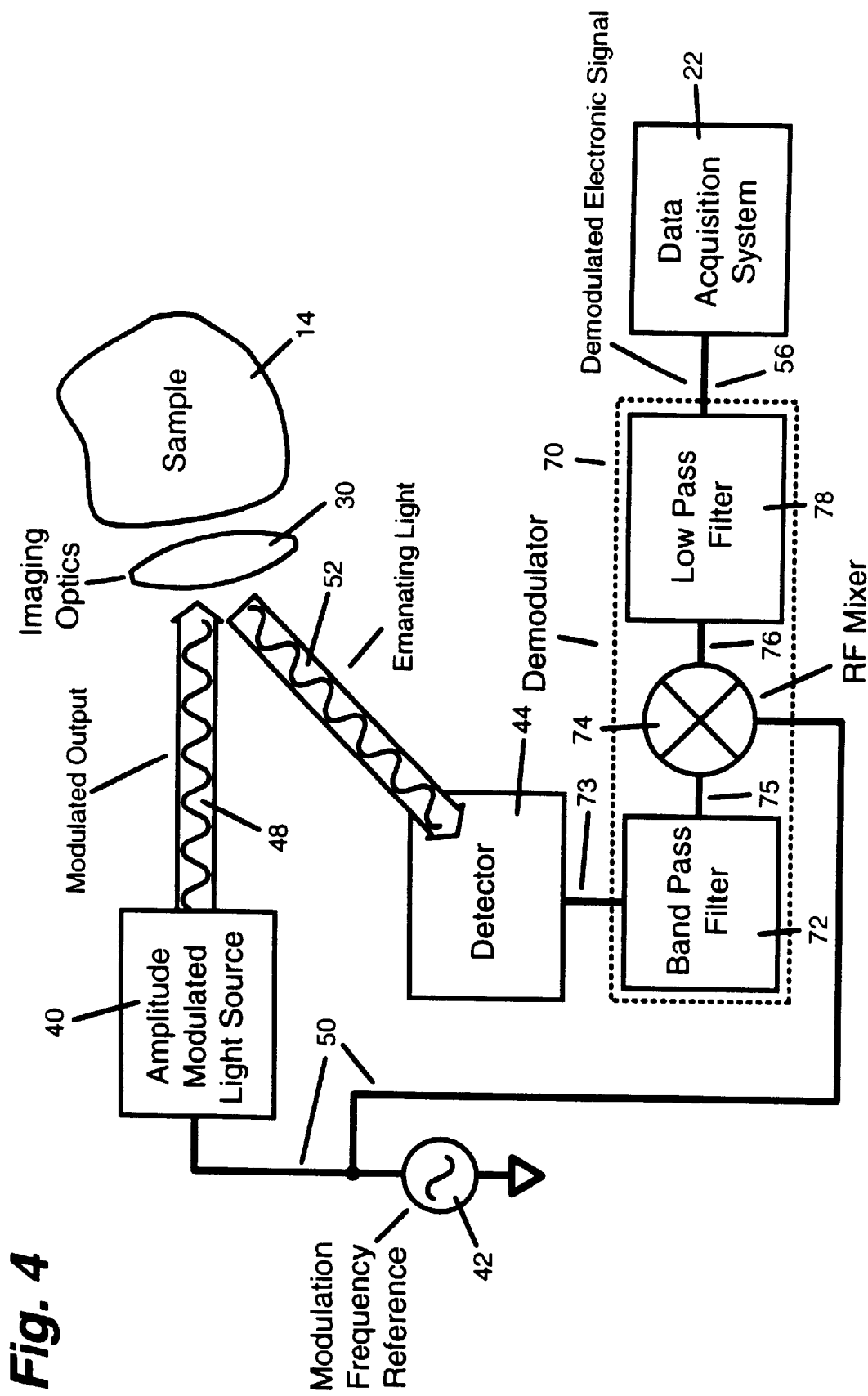
FIG. 4 illustrates use of a simple heterodyne demodulator in the present invention.

To illustrate this approach, the inventors of the present invention have further modified the two-photon laser scanning imaging system described in Example 2. Instead of using a commercial high-frequency lock-in amplifier as the demodulator, a simple heterodyne demodulator 70 was constructed, as illustrated in FIG. 4. This demodulator had: a narrow bandwidth band pass filter 72, having a center frequency at the modulation frequency (i.e., 80 MHz), which was used to reduce excess bandwidth of the detector signal 73 prior to mixing; a radiofrequency (RF) mixer 74, such as a double-balanced mixer, which was used to mix the band pass filtered detector signal 75 with the modulation reference signal 50 so as to produce a sum and difference mixer signal 76; and a low pass filter 78, which was used to filter the mixer signal 76, removing the unwanted sum component from the mixer signal and any excess noise signals beyond the desired bandwidth of the data acquisition system 22, prior to data acquisition. As in the previous examples, demodulation prior to data acquisition caused background noise and other interference, such as contamination of the detector signals from ambient room light, to be electronically rejected.

Data from this Example for the apparatus and method described above are also shown in TABLE 1, which compares imaging results obtained using an inherently modulated laser light source (modulated at 80 MHz) and the heterodyne demodulator illustrated in FIG. 4 with that obtained using conventional dc or direct detection. Data was collected under conditions of moderate, continuous optical background (DC Background). As in previous examples, a clear advantage is evident for the modulated apparatus, particularly in the presence of background. Similar results were obtained for both approaches in the absence of background (data not shown).

Thus, this example further illustrates that the performance of new or existing imaging devices and systems, such as, for example, the two-photon laser scanning microscope or other imaging systems, can be significantly enhanced by incorporation of the modulation and demodulation methods and apparatus of the present invention.

Note that in addition to the heterodyne demodulator illustrated here, related superheterodyne demodulators may also be used, especially if the modulation frequency of the light source is expected to vary substantially from the specific, optimized design frequency of the demodulator. Such superheterodyne apparatus are more optimally suited to narrow band detection of signals at frequencies that may be substantially different than that of a single design frequency, such as, for example, within the range of 50–150 MHz.

Example 4—Use of Quadrature Heterodyne Demodulators

The simple single channel demodulators described in Examples 1–3 require that the phase of the detector signal be carefully adjusted relative to that of the modulation reference signal so as to maximize demodulated electronic signal magnitude and minimize or eliminate potential phase errors in the demodulated signals. Such phase errors can result in a spuriously bipolar demodulated electronic signal that may needlessly complicate interpretation of image data, Example complications include non-zero backgrounds, dc image offsets, and image inversion and other aliasing phenomena. Normally, such phase matching can be accomplished by use of a simple phase correction process it the outset of an imaging session (for example, by maximizing the demodulated electronic signal magnitude or image contrast using a uniform reference sample). However, methods and apparatus capable of automated phase matching may often be desirable. Commercial dual-phase lock-in amplifiers, for example, are capable of such automated phase matching, but as addressed earlier, such an approach is less than optimal due to potential expense and performance compromises.

Wachter et al. (Int. J. Mass Spectrom, Ion Proc., 103 (1991) 169; and U.S. Pat. Nos. 5,745,437 and 5,889,490) teach various simple quadrature (also known as dual-phase) demodulation methods that are applicable to such automated phase matching. Specifically, the present inventors have found that such quadrature methods are well suited to the field of optical imaging, and more specifically to implementation of the present invention in such field.

Figure 5:
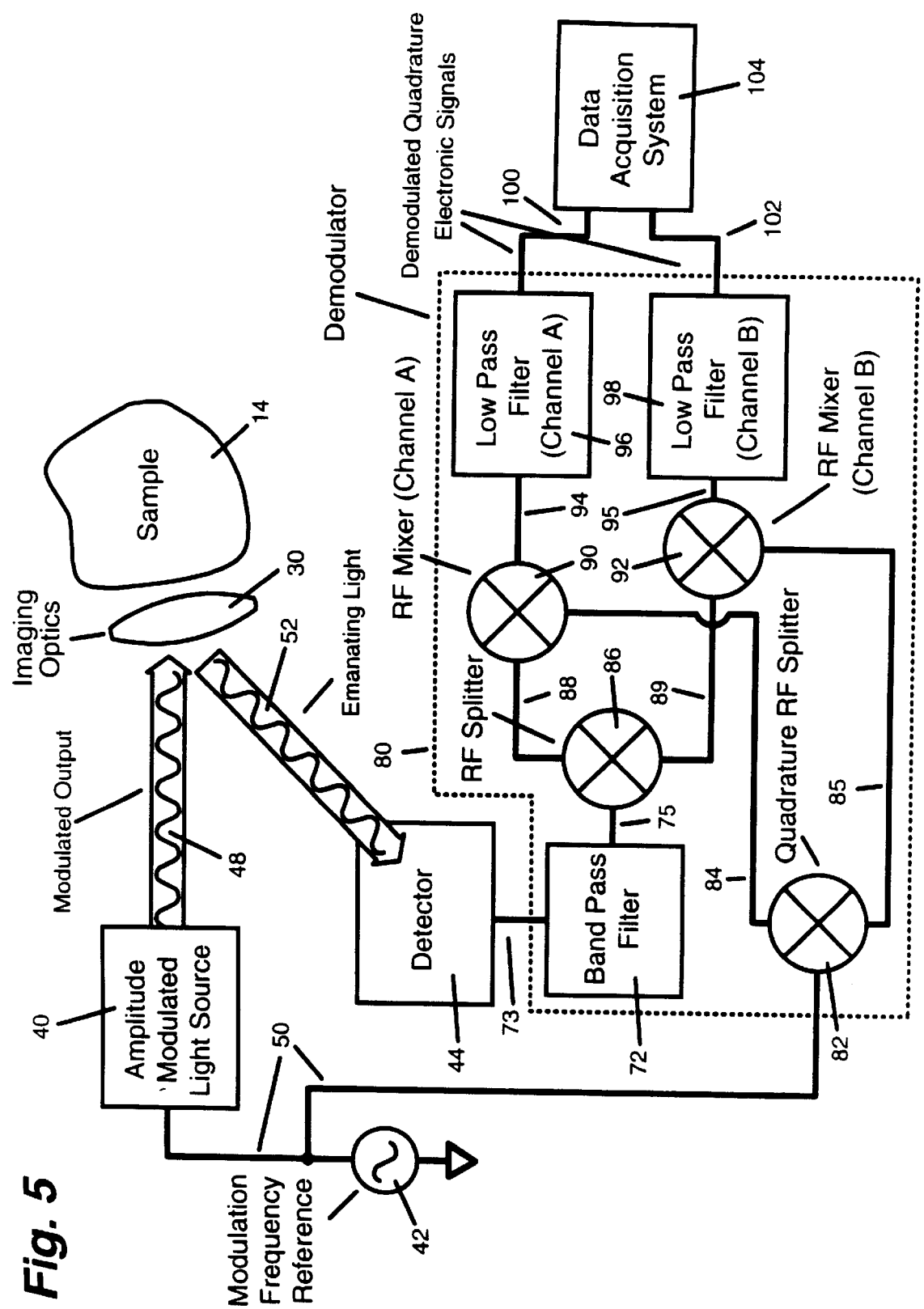
FIG. 5 illustrates use of a simple quadrature heterodyne demodulator in the present invention.

To illustrate this approach, the inventors of the present invention have further modified the two-photon laser scanning imaging system described in Example 3. In particular, instead of using a single channel heterodyne demodulator 70, a dual-channel, quadrature heterodyne demodulator 80 was constructed, as illustrated in FIG. 5. This modified demodulator had the following: a quadrature RF splitter 82 functioning on the modulation reference signal 50 so as to split the reference signal 50 into two orthogonal components (i.e., Channel A and Channel B reference signals, 84 and 85, respectively);

a narrow bandwidth band pass filter 72 having a center frequency at the modulation frequency;

a RF splitter 86 functioning on the band pass filter output signal 75 so as to split this signal into two substantially equal components (i.e., Channel A and Channel B signals, 88 and 89, respectively);

dual RF mixers (RF Mixers for Channel A and Channel B, 90 and 92, respectively), such as double-balanced mixers, used to mix the Channel A (88) and Channel B (89) signals, respectively, with the Channel A (84) and Channel B (85) reference signals, respectively, so as to produce two pairs of sum and difference mixer signals, 94 and 95, respectively; dual low pass filters (Channel A and Channel B, 96 and 98, respectively) used to filter the respective Channel A and Channel B mixer signals 94, 95, thereby producing dual demodulated quadrature electronic signals, 100 and 102, respectively; and a dual-channel data acquisition system 104 capable of simultaneous or substantially simultaneous sampling of the dual demodulated quadrature electronic signals, 100, 102. By capturing quadrature data using such a system, images may be phase corrected during acquisition, or at a later time, using common phase correction algorithms. Signal to noise performance of such a system is comparable to that of the heterodyne system described in Example 3. Furthermore, such a system is immune to phase mismatch between detector signals and modulation reference signals.

Thus, this example further illustrates that the performance of new or existing imaging devices and systems, such as, for example, the two-photon laser scanning microscope or other imaging systems, can be significantly enhanced by incorporation of the modulation and demodulation methods and apparatus of the present invention. Note that in addition to the quadrature heterodyne demodulator illustrated here, related quadrature superheterodyne demodulators may also be desirable, especially if the modulation frequency of the light source can vary substantially from an optimized design frequency.

It will be clear from the preceding examples and embodiments that the present invention may find use in, for example: various single-photon, two-photon and multiphoton excited microscopes and optical imaging devices and systems based on transmission, absorption, reflection, scatter or luminescence based phenomena; laser scanning microscopes; confocal microscopes; optical coherence tomography systems; terahertz imaging systems; and various scanning probe optical microscopes. The present invention is also applicable to optical or imaging system configurations, such as confocal detection, parafocal detection, monostatic detection, bistatic detection, descanned detection, whole area detection, external detection, and non-optical detection. Further, while the examples provided herein have, for the sake of clarity, focused primarily on amplitude modulation, the present invention can also be used with other modulation methods, such as phase modulation and frequency modulation, and other modulation sources, such as phase modulated light sources and frequency modulated light sources. Furthermore, the present invention is applicable to other demodulation methods, such as single-sideband (SSB) demodulation and second-harmonic detection, will also be applicable to the present invention. Moreover, simultaneous or substantially simultaneous modulation and demodulation at several modulation frequencies, for example to multiplex simultaneous illumination and detection at several locations on a sample, and such as those taught in Wachter et al. (U.S. Pat. Nos. 5,745,437 and 5,889,490), can also be used in the present invention.

It will be understood that each of the elements described above, or two or more together, may also find useful application in other types of constructions or applications differing from the types described above but which are fully intended to be included within the present invention.

While the present invention has been illustrated and described using specific examples and embodiments of methods and apparatus for improved optical imaging, the present invention is not intended to be limited to the details shown, since it will be understood that various omissions, modifications, substitutions and changes in the forms and details of the methods and apparatus illustrated, and in their operation, can be made by those skilled in the art without departing in any way, from the spirit of the present invention. For instance, in the third example, certain details of the modulation and demodulation apparatus may be omitted or changed to produce a more simple imaging apparatus (such as, for example, omitting one or more bandpass filters, using integrated circuit demodulators, using different modulation frequencies, and so on), although such modification may yield an overall reduction in imaging performance.

TABLE 1

Example Data Comparing Imaging Results (Signal-to-Noise Ratio, $(S-B)/N_B$), for Various Example Apparatus Data presented for Example 1 illustrates data for performance for an extracavity modulated laser light source (modulated at 47 kHz) and demodulation versus that obtained using conventional dc or direct detection, under conditions of (1) no optical background and (2) moderate to severe, continuous optical background (DC Background). In both cases, significant advantage is noted for the modulated apparatus, and particularly in the presence of background.

Data presented for Example 2 provides a similar illustration for an inherently modulated laser light source (modulated at 70 MHz). Similar results are obtained in the absence of background, but a clear advantage is evident for the modulated apparatus in the presence of background. Note that in this example, the DC Background level used is considerably lower than that used in Example 1.

Example 3 provides a similar illustration for an inherently modulated laser light source (modulated at 80 MHz). As in previous examples, a clear advantage is noted for the modulated apparatus in the presence of background. The DC Background level used is comparable to that used in Example 2.

| Config-uration | Experimental Conditions | $(S - B)/N_B$ | |
|---|---|---|---|
| | | No Background | DC Background |
| Example 1 | No Modulation | 188 | 0.005 |
| | Modulated (47 kHz) | 340 | 2.2 |
| Example 2 | No Modulation | 192 | 5.5 |
| | Modulated (70 MHz) | 137 | 94.0 |
| Example 3 | No Modulation | | 5.7 |
| | Modulated (80 MHz) | | 156 |

What is claimed as new and desired to be protected by Letters Patent is set forth in the appended claims:

1. A method for imaging a material, the method comprising the steps of:
   encoding light from a light source with a modulation pattern to produce a modulated light;
   directing said modulated light onto or into said material, said material emitting a modulated optical signal which is characteristic of the material;
   detecting said emitted modulated optical signal from said material and converting said optical signal into a modulated electronic signal which is characteristic of the material; and
   demodulating the modulated electronic signal which is characteristic of the material.

2. The method according to claim 1 wherein said light from said light source is encoded with a modulation pattern produced by said light source.

3. The method according to claim 1 wherein said light from said light source is encoded with a modulation pattern synchronous with a modulation frequency reference signal and wherein said modulation frequency reference signal is used in demodulating said modulated electronic signal.

4. The method according to claim 1 wherein said modulation frequency reference signal is produced using a modulation frequency reference.

5. The method according to claim 1 wherein said imaging is for microscopy.

6. The method according to claim 1 wherein said imaging is for medical imaging.

7. The method according to claim 1 further comprising the step of collecting the demodulated electronic signal and forming a multi-dimensional image of said material.

8. The method according to claim 1, wherein said detecting of said emitted modulated optical signal uses detection selected from the group consisting of confocal detection, parafocal detection, monostatic detection, bistatic detection, descanned detection, whole area detection, external detection, and non-optical detection.

9. The method according to claim 1, wherein said encoding and said demodulation are performed simultaneous or substantially simultaneous at two or more modulation frequencies.

10. A method for imaging a material, the method comprising the steps of:
    producing a reference frequency signal;
    encoding light from a light source with a modulation pattern synchronous with said reference frequency signal to produce a modulated light;
    directing said modulated light onto or into said material, said material emitting a modulated optical signal resulting from an interaction of said modulated light and said material;
    detecting said emitted modulated optical signal and converting said optical signal into a modulated electronic signal which is characteristic of the material; and
    demodulating the modulated electronic signal using said reference frequency signal to produce a demodulated electronic signal which is characteristic of the material.

11. The method according to claim 10 wherein said imaging is for microscopy.

12. The method according to claim 10 wherein said imaging is for medical imaging.

13. The method according to claim 10 further comprising the step of collecting the demodulated electronic signal and forming a multi-dimensional image of said material.

14. The method according to claim 10, wherein said detecting of said emitted modulated optical signal uses detection selected from the group consisting of confocal detection, parafocal detection, monostatic detection, bistatic detection, descanned detection, whole area detection, external detection, and non-optical detection.

15. The method according to claim 10, wherein said encoding and said demodulation are performed simultaneous or substantially simultaneous at two or more modulation frequencies.

16. A method for microscopic imaging, the method comprising the steps of:
    producing a reference frequency signal;
    encoding light from a light source with a modulation pattern synchronous with said reference frequency signal to produce a modulated light;
    directing said modulated light onto or into a material to be imaged, said material emitting a modulated optical signal resulting from an interaction of said modulated light and said material;
    detecting said emitted modulated optical signal and converting said optical signal into a modulated electronic signal which is characteristic of the material; and demodulating the modulated electronic signal using said reference frequency signal to produce a demodulated electronic signal which is characteristic of the material.

17. The method according to claim 16 further comprising the step of collecting the demodulated electronic signal and forming a multi-dimensional image of said material.

18. The method according to claim 16, wherein said detecting of modulated light uses detection selected from the group consisting of confocal detection, parafocal detection, monostatic detection, bistactic detection, descanned detection, whole area detection, external detection, and non-optical detection.

19. The method according to claim 16, wherein said encoding and said demodulation are performed simultaneous or substantially simultaneous at two or more modulation frequencies.

* * * * *